United States Patent
Heiniger et al.

(10) Patent No.: US 7,744,565 B2
(45) Date of Patent: *Jun. 29, 2010

(54) APPARATUS FOR SUBCUTANEOUS ADMINISTRATION OF AN INJECTABLE PRODUCT

(75) Inventors: Hanspeter Heiniger, Lotzwil (CH); Guido Hertig, Mattstetten (CH)

(73) Assignee: TecPharma Licensing AG, Burgdorf (CH)

( * ) Notice: Subject to any disclaimer, the term of this patent is extended or adjusted under 35 U.S.C. 154(b) by 48 days.

This patent is subject to a terminal disclaimer.

(21) Appl. No.: 11/342,949

(22) Filed: Jan. 30, 2006

(65) Prior Publication Data

US 2006/0184134 A1    Aug. 17, 2006

Related U.S. Application Data

(63) Continuation of application No. 09/589,384, filed on Jun. 7, 2000, now Pat. No. 7,074,211.

(30) Foreign Application Priority Data

Jun. 7, 1999    (DE)    ................ 199 25 904

(51) Int. Cl.
 A61M 5/00    (2006.01)
 A61M 5/32    (2006.01)
(52) U.S. Cl. .............. 604/117; 604/192; 604/110; 604/187
(58) Field of Classification Search ........... 604/110, 604/187, 263, 117, 171, 192, 198, 207, 208, 604/134, 135, 137
See application file for complete search history.

(56) References Cited

U.S. PATENT DOCUMENTS

| | | | |
|---|---|---|---|
| 2,531,267 A | 11/1950 | Harnisch | |
| 2,664,086 A | 12/1953 | Transue | |
| 3,605,744 A | 9/1971 | Dwyer | |
| 3,677,245 A | 7/1972 | Welch | |
| 4,445,510 A | 5/1984 | Rigby | |
| 4,946,446 A | 8/1990 | Vadher | |
| 4,973,318 A | 11/1990 | Holm et al. | |
| 5,092,842 A | 3/1992 | Bechtold et al. | |
| 5,114,406 A | 5/1992 | Gabriel et al. | |
| 5,171,231 A | 12/1992 | Heiliger | |
| 5,209,739 A | 5/1993 | Talalay | |
| 5,244,465 A | 9/1993 | Michel | |
| 5,273,544 A | 12/1993 | van der Wal | |
| 5,292,314 A | 3/1994 | D'Alessio et al. | |
| 5,320,609 A | 6/1994 | Haber et al. | |
| 5,337,756 A | 8/1994 | Barbier et al. | |
| 5,338,311 A | 8/1994 | Mahurkar | |

(Continued)

FOREIGN PATENT DOCUMENTS

DE    1491841    7/1969

(Continued)

*Primary Examiner*—Kevin C Sirmons
*Assistant Examiner*—Catherine N Witczak
(74) *Attorney, Agent, or Firm*—Dorsey & Whitney LLP; David E. Bruhn

(57) ABSTRACT

An apparatus for subcutaneous administration of an injectable product including a housing, a container for the product to be injected, an injection needle and a needle protection sleeve surrounding the injection needle, wherein the apparatus also includes an indicator to tell a user when the needle protection sleeve has attained its maximum distal position.

10 Claims, 1 Drawing Sheet

U.S. PATENT DOCUMENTS

| | | |
|---|---|---|
| 5,472,430 A | 12/1995 | Vaillancourt et al. |
| 5,514,097 A | 5/1996 | Knauer |
| 5,527,294 A | 6/1996 | Weatherford et al. |
| 5,540,664 A | 7/1996 | Wyrick |
| 5,549,558 A | 8/1996 | Martin |
| 5,573,510 A | 11/1996 | Isaacson |
| 5,591,138 A | 1/1997 | Vaillancourt |
| 5,629,299 A | 5/1997 | Brown et al. |
| 5,634,906 A * | 6/1997 | Haber et al. ............. 604/136 |
| 5,643,214 A | 7/1997 | Marshall et al. |
| 5,658,259 A | 8/1997 | Pearson et al. |
| 5,674,203 A | 10/1997 | Lewandowski |
| 5,779,677 A | 7/1998 | Frezza |
| 5,800,390 A | 9/1998 | Hayakawa et al. |
| 5,873,856 A | 2/1999 | Hjertman et al. |
| 5,957,897 A | 9/1999 | Jeffrey |
| 6,090,080 A | 7/2000 | Jost et al. |
| 6,277,098 B1 * | 8/2001 | Klitmose et al. ........... 604/207 |
| 6,287,283 B1 | 9/2001 | Ljunggreen et al. |
| 6,547,764 B2 | 4/2003 | Larsen et al. |
| 6,626,864 B2 * | 9/2003 | Jansen et al. ............. 604/110 |
| 2004/0006285 A1 | 1/2004 | Douglas et al. |

FOREIGN PATENT DOCUMENTS

| | | |
|---|---|---|
| DE | 3638984 | 5/1988 |
| DE | 4223959 | 1/1993 |
| DE | 3645245 | 1/1994 |
| EP | 0516473 | 2/1996 |
| FR | 1409793 | 7/1965 |
| FR | 2700960 | 8/1994 |
| WO | WO 9110460 | 7/1991 |
| WO | WO 9305835 | 4/1993 |
| WO | WO 9409841 | 5/1994 |
| WO | WO 9925400 | 5/1999 |
| WO | WO 9822031 | 11/1999 |

* cited by examiner

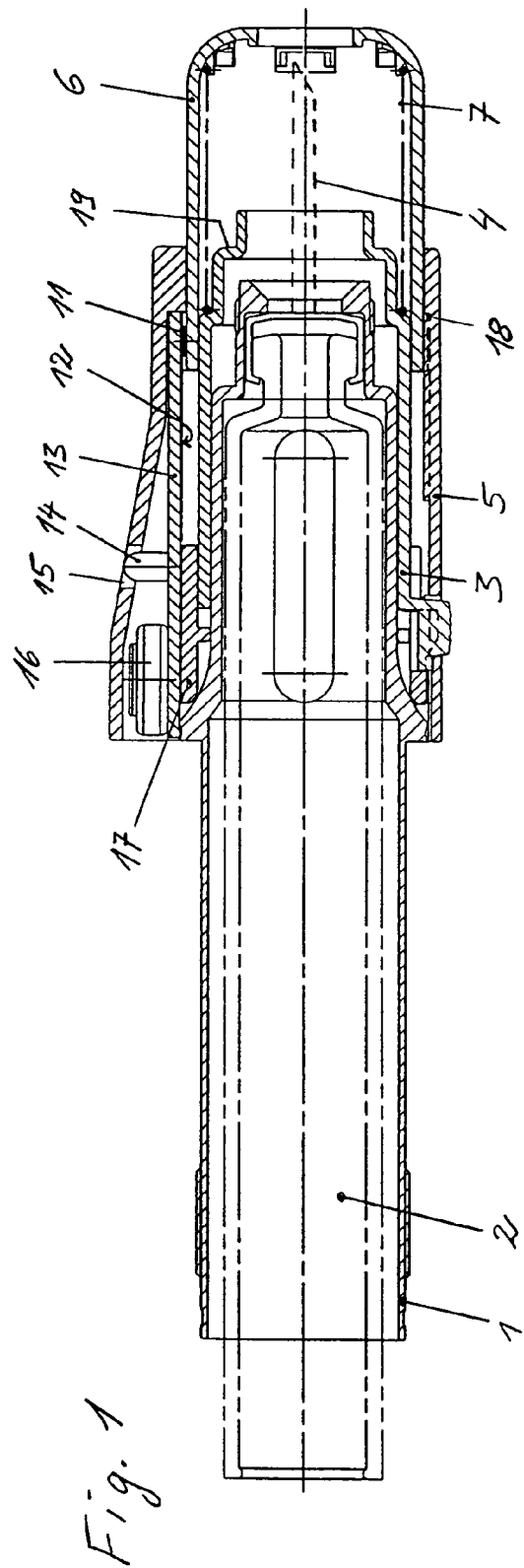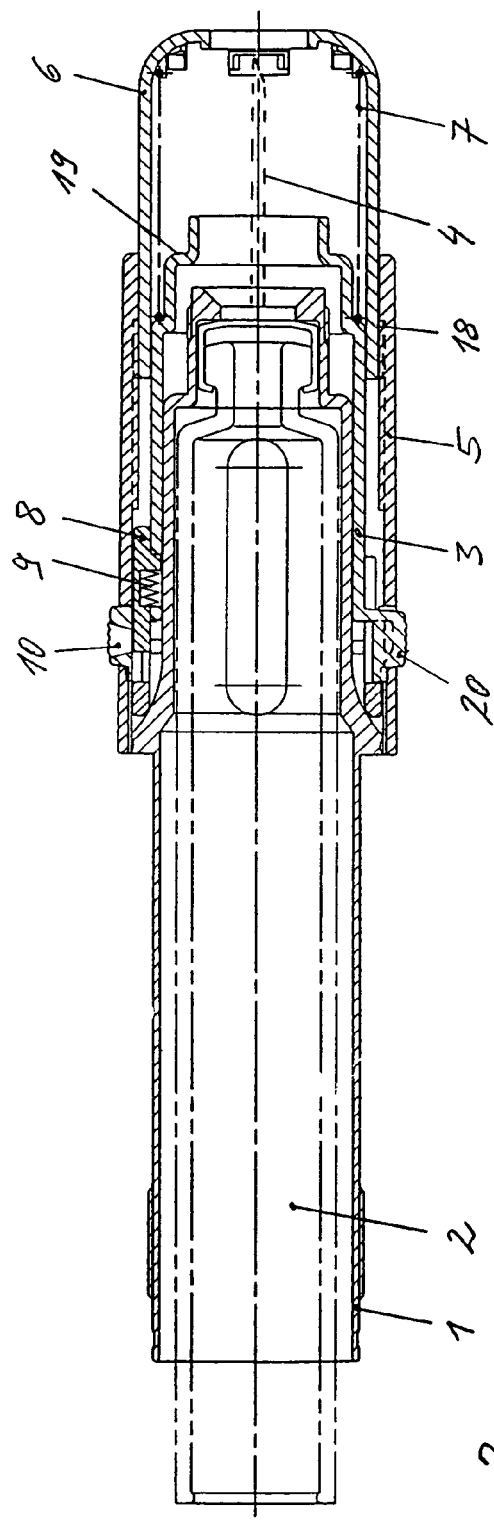

APPARATUS FOR SUBCUTANEOUS ADMINISTRATION OF AN INJECTABLE PRODUCT

CROSS REFERENCE TO RELATED APPLICATION(S)

This application is a continuation of U.S. application Ser. No. 09/589,384, filed on Jun. 7, 2000, which claims priority to German patent application No. 199 25 904.6 filed Jun. 7, 1999, the contents of both of which are incorporated herein in their entirety by reference.

BACKGROUND

The present invention relates to an apparatus for subcutaneous administration of an injectable product, the apparatus comprising an injection needle and a needle protection sleeve surrounding the injection needle. For pricking with the injection needle, the needle protection sleeve is shifted so that the injection needle protrudes from the needle protection sleeve.

Injection apparatuses including needle protection sleeves are known, for example, from DE 198 22 031. Such a needle protection sleeve totally conceals the injection needle or at least conceals it to such an extent that a user of the apparatus, for instance in administering the product himself, no longer has the possibility of checking whether the injection needle after piercing the skin has also actually attained the desired piercing depth in the tissue under the skin.

SUMMARY

An object of the present invention is to provide a means for checking the penetration of the needle of an apparatus for subcutaneous administration of an injectable product.

This object is addressed by an injection apparatus comprising an indicator which indicates to a user of the apparatus that a needle protection sleeve associated with the apparatus is in its distal position.

The present invention relates to an apparatus for subcutaneous administration of an injectable product comprising at least one housing, a product container, an injection needle for administering the product and a needle protection sleeve surrounding the injection needle. The container is accommodated in or on the housing. The injection needle is connected to the container and protrudes beyond the housing. The needle protection sleeve is longitudinally, reciprocatingly shiftably connected to the housing between a proximal position and a distal position. In the distal position of the needle protection sleeve, the injection needle for subcutaneous administration of the product protrudes sufficiently beyond the needle protection sleeve, whereas, in the proximal position, the injection needle does not protrude beyond the needle protection sleeve, the needle protection sleeve protruding somewhat beyond the injection needle. The injectable product is preferably a medicinal active liquid substance as administered by a user of the apparatus himself, for example, within the scope of a treatment, a prominent example of such an active substance solution being insulin.

In accordance with the present invention, the apparatus comprises an indicator which on insertion of the injection needle and a retraction of the needle protection sleeve involved, indicates to the user whether, or that, the needle protection sleeve has attained its distal position.

The indicator may be formed by at least one marking provided on the housing or needle protection sleeve arranged so as to be visible to the user upon insertion and indicating in conjunction with the needle protection sleeve the travel from the proximal position of the needle protection sleeve and, thus, the pricking depth of the injection needle.

In one embodiment, the injection apparatus includes a needle protection sleeve which is retractable into the housing. This is advantageous because the movement of the sleeve cannot be obstructed by the hand or the fingers of the user holding of the apparatus. In this embodiment, a marking is applied to the needle protection sleeve. When the distal position of the needle protection sleeve is attained, the marking becomes visible through a window in the housing. Serving as such a marking is more particularly a rear, i.e. distal, edge of the needle protection sleeve or a clearly discernible marking strip applied to the outer shell surface of the needle protection sleeve preferably circumferentially, preferably forming the distal edge. In principle, the circumferential marking strip can also be applied to a proximal edge of the needle protection sleeve so that the user, for example, is able to observe the disappearance of the strip in the housing.

In one embodiment, an injection apparatus in accordance with the present invention includes an indicator which is actuated by the needle protection sleeve when it is shifted into the distal position. This feature of actuating the indicator enhances user convenience and safety when handling the apparatus. The user more particularly does not need to first consider whether, for example, a no longer visible marking means that the desired pricking depth is achieved. When the distal position is reached, this is clearly indicated. Likewise, the explicit indication may show that the desired pricking depth is yet to be reached.

In some embodiments, the indicator is held by the housing, i.e. arranged in or on the housing.

Attaining the distal position of the needle protection sleeve may be signalled audibly or, advantageously, visibly. A visible indication is arranged on the apparatus where it is immediately in view, more particularly arranged at a clearly visible level relative to the longitudinal centerline of the apparatus, preferably aligned with the needle. Such an arrangement is directly achieved by a display which is not simultaneously an integral component of the needle protection sleeve, rather, is formed by means of a component separate therefrom.

In accordance with one exemplary embodiment, the indicator is actuated by the needle protection sleeve via a transfer member. In this arrangement, the transfer member is preferably formed by a switch in an electric or optic circuit. The switch is more preferably a contactless switch, for example a Hall generator.

In another exemplary embodiment of an actuatable indicator, the needle protection sleeve does not first act via one or more transfer members, but directly on the indicator. In this exemplary embodiment, the indicator comprises a slider or a slide including an optical marking clearly visible to the user in a window of the housing when the needle protection sleeve has attained its distal position. The slider is mounted on the housing slidable in the shifting direction of the needle protection sleeve against the return force of a return element. Upon insertion of the injection needle, the needle protection sleeve is urged against the slider which is shifted by the urging of the needle protection sleeve and against the force of the return element together with the needle protection sleeve. The return element returns the slider to its starting position when it is no longer urged by the needle protection sleeve. By configuring the slider sufficiently long and arranging the marking on the slider, the marking reaches the eye of the user as close as possible. Also advantageously provided on the slider is a marking which explicitly indicates the state at which the desired pricking depth has not yet been reached.

BRIEF DESCRIPTION OF THE DRAWINGS

FIG. 1 is a longitudinal section through one exemplary embodiment of a means for checking penetration; and FIG. 2 is a longitudinal section through a second exemplary embodiment of a means for checking penetration.

DETAILED DESCRIPTION

FIG. 1 illustrates a longitudinal section through a front part of an apparatus for subcutaneous administration of an injectable product. The apparatus involved is an injection pen of the type that may be used for administering insulin within the framework of diabetes treatment, but other uses are encompassed, too.

Accommodated in a container holder 1 is a container 2 in the form of an ampoule. Such containers 2 and container holders 1 are known in injection pens, for example for insulin administration. Protruding through a front opening of the container holder 1 in a proximal direction is an injection needle 4. The injection needle 4 is connected to an outlet of the container 2, it being through the injection needle that the product contained in the container is delivered in the course of an injection or several injections.

Snugly fitted to the proximal portion of the container holder 1 is a sleeve 3. Likewise, snugly fitted to the front portion on the container holder 1 and latched in place thereon is a further sleeve 5. The container holder 1 and the two sleeves 3 and 5 are arranged concentric to each other, the sleeve 5 thereby surrounding the sleeve 3. The sleeve 3 is thus termed in the following the inner sleeve 3 and the sleeve 5, the outer sleeve 5.

The outer sleeve 5 surrounds the inner sleeve 3 by a clearance so that an annular gap remains between the sleeves 3 and 5. Between the inner sleeve 3 and the outer sleeve 5 shiftably mounted in this annular gap is a needle protection sleeve 6. The needle protection sleeve 6 comprises a plain circular cylindrical shell having at its proximal end, a bottom with an opening for the injection needle 4. The needle protection sleeve is shiftable from a proximal position as shown in FIG. 1 and FIG. 2 in which it protrudes beyond the tip of the injection needle 4, into a distal position into the annular gap between the inner sleeve 3 and outer sleeve 5 until coming up against a stop 19 formed by the inner sleeve 3 against the force of a return element 7. The return element 7 acts between the housing and the needle protection sleeve 6 and serves to elastically return the needle protection sleeve 6 into the proximal position. The return element 7 is formed preferably by a compression spring. The return element 7 is supported at one face end at a circumferential shoulder of the inner sleeve 3 and is urged against the bottom of the needle protection sleeve 6. In their distal portions, the sleeves 3 and 5 are additionally mutually supported by means of a supporting element 17.

In the proximal position of the needle protection sleeve 6 as shown, the needle protection sleeve 6 abuts against a shoulder, configured at the outer sleeve 5 and protruding radially inwards, by a cam 18 jutting outwards from its shell surface area. This prevents the needle protection sleeve 6 from falling out or from being accidentally removed.

Arranged at an outer shell surface area of the needle protection sleeve 6 in a distal position of the needle protection sleeve 6 is a first switching element 11. The first switching element 11 is a permanent magnet. Cooperating with the first switching element 11 is a second switching element 12. The second switching element 12 is formed by a tab of an electrically conductive material. The second switching element 12 extends opposite the first switching element 11 in the shifting direction of the needle protection sleeve 6 along the travel of the needle protection sleeve 6 and thus also of the first switching element 11. The second switching element 12 extends over a length which is at least as long as the length of the travel of the first switching element 11.

The second switching element 12 is arranged at a mounting strip serving as a mounting structure 13, this mounting strip extending in the shifting direction of the needle protection sleeve 6 between the needle protection sleeve 6 and the outer sleeve 5. In this assembly position, the mounting structure 13 is supported and fixed by the supporting element 17 in the housing of the apparatus. Fixing it in place in this assembly position would also be possible by other means, for example simply by means of one of the sleeves 3 and 5 or in cooperation with both sleeves 3 and 5.

The first switching element 11 and second switching element 12 form a Hall generator. This Hall generator is a switch in an electric circuit comprising a luminous element 14 in the form of an LED, a battery 16 for the power supply, conductor means needed to close the circuit and the switch as described above in the circuit.

The circuit is opened and closed by the switch formed by the switching elements 11 and 12. The switch is open as long as the needle protection sleeve 6 is not in its distal position, the luminous element 14 in this switching condition being OFF. As soon as the needle protection sleeve 6 has attained the distal position, the switch closes the circuit and the luminous element 14 is ON. The needle protection sleeve 6 is in its distal position when it has been retracted relative to the housing and the injection needle 4 from its proximal position to such an extent that the injection needle 4 sufficiently protrudes therefrom that the desired pricking depth is attainable for an injection. In the example embodiment, the distal position of the needle protection sleeve 6 coincides with the stopped position of the needle protection sleeve 6 at the stop element of the inner sleeve 3. However, more preferably, the distal position may also be located just a little upstream of the stopped position to ensure particularly reliable switching-over.

In some embodiments the luminous element 14 may comprise a two-color luminous element so that the color of the luminous element 14 illuminated at the time depends on whether the needle protection sleeve 6 is in its distal position or not. In this embodiment, two electric circuits exist, i.e. one for each color, which are open or closed alternatively and depending on the position of the needle protection sleeve 6, namely the position of the first switching element 11, mounted therein, with respect to that of the second switching element 12, i.e., the one circuit being closed when the other is open. A luminous element 14 separate for each color may be provided or a luminous element 14 configured integrally as a multicolor element. A further switch may be provided for activating the power supply only immediately for use of the apparatus.

The distal position of the needle protection sleeve 6 is indicated for example by the color green being lit, while any position prior to the distal position being attained is assigned the color red, although, of course, assigning other colors is just as possible. The color or pair of colors is advantageously selected depending on the configuration of the luminous element so that the color is clearly evident and, when use is made of several colors, these colors in addition being easily distinguishable from each other.

By arranging the circuit or circuits including the second switching element 12, luminous element 14 and battery 16 on an individual, separate mounting structure 13, assembling the indicator and the means required therefor in or on the housing is particularly simple.

The indicator including all circuit elements belonging thereto is protectively enclosed by the outer sleeve 5. The outer sleeve 5 comprises in its shell portion above the luminous element 14 a window 15 through which the luminous element 14 is clearly visible.

Referring now to FIG. 2, there is illustrated, in a longitudinal section, a mechanical means of checking the penetration for the same or generally similar injection pen as that shown in FIG. 1. Unless having to do only with the embodiment shown in FIG. 2, all components alike in function, form and mutual configuration are identified by the same reference numerals (as in FIG. 1). Except for the indicator, only the outer sleeve 5 has a shape different to that of the outer sleeve 5 as shown in FIG. 1, this being due to the fact that the outer sleeve 5 of the second exemplary embodiment accommodates and protects no battery and no luminous element as is the case in FIG. 1.

In a distal portion of the annular gap between the inner sleeve 3 and the outer sleeve 5 at the location of the stop element 17 in the first exemplary embodiment, a slider 8 is accommodated reciprocatingly in the shifting direction of the needle protection sleeve 6. The slider 8 is urged by an elastic-acting return element 9, preferably in the form of a compression spring, into its proximal position as shown in FIG. 2 in which it comes up against a rear face end of the inner sleeve 3. When urged by the needle protection sleeve 6 being retracted to its distal position, the slider 8 is shifted back against the elastic return force of the return element 9, the slider 8 being shiftable up to a stop of the housing, as a result of which, at the same time, the retraction of the needle protection sleeve 6 is limited. The return element 9 is received in a recess of the slider 8. This recess is formed in an inner shell surface area of the slider 8. The return element 9 is tensioned between two opposite surface areas, one of which is formed on the slider 8 and the other on the housing.

Provided in the shell surface area of the outer sleeve 5 above the slider 8 is a window. Arranged or inserted in this window is a lens 10 acting as a magnifying glass. Applied to an outer surface area facing the outer sleeve 5 on the slider 8 is a marking which rests under the lens 10 when the needle protection sleeve 6 has assumed its distal position. In the exemplary embodiment shown in FIG. 2, an indicator is thus formed by the slider 8 and the marking applied thereto and a window in the non-shiftable outer sleeve 5, the marking and the window coinciding in the distal position of the needle protection sleeve 6. The slider 8 may also serve as a whole as a marking, its appearance under the window then indicating the distal position of the needle protection sleeve 6. Both apparatuses as shown in FIGS. 1 and 2 permit adjustment of the pricking depth of the injection needle by changing the retraction depth of the needle protection sleeve 6. Changing the retraction depth occurs by shifting the inner sleeve 3 and thus the stop 19 formed by the inner sleeve 3. Shifting the inner sleeve 3 is effectuated by turning the outer sleeve 5. To longitudinally shift the inner sleeve 3 and thus shift the stop 19, the inner sleeve 3 protrudes through the outer sleeve 5 by means of an adjusting member 20 molded to the inner sleeve 3. The adjusting member 20 engages the outer sleeve 5 such that turning the outer sleeve 5 results in shifting of the adjusting member 20 and thus also shifting of the inner sleeve 3. In this arrangement, the slider 8 is permanently held in contact with the inner sleeve 3 by means of the return element 9 so that it is always correctly positioned with respect to the needle protection sleeve 6 in every shifting position of the inner sleeve 3. Preferably, the lens 10 is also shifted with the inner sleeve 3, preferably without changing its position relative to the slider 8.

In the foregoing description, preferred embodiments of the invention have been presented for the purpose of illustration and description. They are not intended to be exhaustive or to limit the invention to the precise form and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

INDEX TO CERTAIN COMPONENTS 1 container holder
2 container
3 inner sleeve
4 injection needle
5 outer sleeve
6 needle protection sleeve
7 return element
8 slider
9 return element
10 lens
11 first switching element
12 second switching element
13 mounting structure
14 indicator, luminous element
15 window
16 battery
17 supporting element
18 cam
19 stop
20 adjusting member

We claim:

1. An apparatus for subcutaneous self-administration of an injectable product comprising:
    a housing;
    a receiving sleeve coupled with the housing;
    an injection needle protruding beyond the housing;
    a needle protection sleeve generally surrounding the injection needle, the needle protection sleeve being connected to the housing and slideable between a proximal position and a distal position, wherein in the distal position the injection needle protrudes beyond the needle protection sleeve and a rear portion of the needle protection sleeve is disposed within an interior of the housing such that a user of the apparatus, when placing the needle protection sleeve on tissue and moving the needle protection sleeve from the proximal position to the distal position, cannot view the needle entering and penetrating the tissue and cannot gauge the relative position of the needle by monitoring the relative movement of the rear portion of the needle protection sleeve, and wherein in the proximal position the injection needle does not protrude beyond the needle protection sleeve;
    an indicator which visibly indicates to the user of the apparatus that the needle protection sleeve is in the distal position during insertion of the injection needle for administration of the injectable product, wherein the needle protection sleeve actuates the indicator; and a window on the housing, wherein the indicator comprises a slider including an optical marker visible through the window when the needle protection sleeve is in the distal position.

2. The apparatus of claim 1, wherein the slider is slideable in a shifting direction.

3. The apparatus of claim 2, wherein movement of the needle protection sleeve from the proximal position to the distal position slides the slider in the shifting direction.

4. The apparatus of claim 1, wherein the slider further includes a second optical marker that indicates when the needle protection sleeve is not in the distal position.

5. The apparatus of claim 1, wherein the housing comprises an outer sleeve and the receiving sleeve comprises an inner sleeve, wherein the outer sleeve surrounds and is spaced from the inner sleeve thereby defining an annular gap, the rear portion of the needle protection sleeve being in the annular gap in the distal position.

6. The apparatus of claim 5, wherein a return element acts between one of the inner sleeve and the outer sleeve at one end and the needle protection sleeve at an opposite end and serves to elastically return the needle protection sleeve into the proximal position.

7. The apparatus of claim 6, wherein the return element is supported at a circumferential shoulder of the inner sleeve and is urged against the needle protection sleeve.

8. The apparatus of claim 5, wherein the inner sleeve forms a stop against which the needle protection sleeve abuts in the distal position.

9. The apparatus of claim 8, wherein a position of the stop relative to the needle protection sleeve is adjustable by an adjusting member formed on the inner sleeve such that the adjusting member adjusts a distance the needle protection sleeve travels to reach the stop.

10. The apparatus of claim 9, wherein the indicator is held in contact with the inner sleeve by a return element and a position of the indicator adjusts with the position of the stop.

* * * * *